(12) United States Patent
Herer et al.

(10) Patent No.: US 7,289,600 B2
(45) Date of Patent: Oct. 30, 2007

(54) APPARATUS AND PROCESS FOR IRRADIATING PRODUCT PALLETS

(75) Inventors: Arnold S. Herer, Pennington, NJ (US); Fréderic Stichelbaut, Mazy (BE)

(73) Assignee: Ion Beam Applications S.A., Louvain-La-Neuve (BE)

(*) Notice: Subject to any disclaimer, the term of this patent is extended or adjusted under 35 U.S.C. 154(b) by 0 days.

(21) Appl. No.: 10/804,605

(22) Filed: Mar. 18, 2004

(65) Prior Publication Data

US 2004/0223870 A1 Nov. 11, 2004

Related U.S. Application Data

(60) Provisional application No. 60/466,210, filed on Apr. 28, 2003.

(30) Foreign Application Priority Data

Mar. 18, 2003 (EP) ............................. 03447055

(51) Int. Cl.
*G21K 5/10* (2006.01)
(52) U.S. Cl. ..................................... 378/69; 378/64
(58) Field of Classification Search ............... 378/64, 378/68, 69
See application file for complete search history.

(56) References Cited

U.S. PATENT DOCUMENTS 4,066,907 A * 1/1978 Tetzlaff ..................... 378/69

6,504,898 B1 * 1/2003 Kotler et al. ............... 378/64
6,763,085 B2 * 7/2004 Hansen et al. .............. 378/69
6,777,692 B2 * 8/2004 Jongen .................... 250/492.1
6,931,095 B1 * 8/2005 Koenck et al. ............. 378/64

FOREIGN PATENT DOCUMENTS

DE    35 33 826 A1    4/1987
WO    01/11634 A1     2/2001

* cited by examiner

*Primary Examiner*—Edward J. Glick
*Assistant Examiner*—Thomas R. Artman
(74) *Attorney, Agent, or Firm*—Fitch, Even, Tabin & Flannery (57) ABSTRACT

The present invention is related to process and an apparatus for irradiating products by means of high energy X-ray beam source (1) in an installation having an irradiation chamber (2), said process comprising the following steps, controlled by controlling means:
  determining the density of the products to be irradiated,
  in order to irradiate said products as a stack predetermining, on the basis of said density, the optimal size of the product stack able to optimize the throughput of the installation and/or the dose uniformity ratio (DUR),
  in the irradiation chamber (2), loading products as a stack onto rotation means (3) located in front of the X-ray beam source (1),
  while rotating the rotation means around a rotation axis (10), irradiating said products from a lateral side of said product stack.

17 Claims, 7 Drawing Sheets

Square pallets

APPARATUS AND PROCESS FOR IRRADIATING PRODUCT PALLETS

FIELD OF THE INVENTION

The present invention is related to a process and an apparatus for irradiating products with a high energy radiation beam, in particular low density products conveyed in the form of pallets, or individual low density bulk or small packages.

A possible application of such apparatus and process is the sterilization of products such as medical devices.

STATE OF THE ART

A widely used sterilization technique for medical devices, used for more than 50 years, is the ethylene oxide (EO) sterilization processing. This process consists essentially in the following steps:

preconditioning wherein the pallets are stored in a room with controlled humidity and temperature, transfer of pallets to the sterilization chamber, sterilization within the chamber where the temperature and humidity are controlled and where ethylene oxide gas is used as the sterilization medium, transfer of pallets to an aeration room (degassing room), aeration of the pallets in the degassing room with controlled temperature and ventilation.

However, the main drawback of this process is related to the use of this very toxic ethylene oxide gas.

In particular, this process must be performed under strictly controlled conditions. Furthermore, the degassing and the aeration period can cover up to several days. Therefore, there is a need for suggesting a process where just-in-time availability of products can be obtained. Moreover, this process is efficient at treating large batches, (i.e. batches corresponding to the size of the sterilization chamber), but is not efficient at treating economically smaller productions, e.g. one or a few pallets.

Another well known sterilization technique is the use of radiation. Electron beam may be used, but because of the limited penetration depth in matter of electrons (a few cm, in unit density material), these are not adapted for the treatment of large volumes such as whole pallets. A better solution is the use of photons, being either gamma rays or X-rays. Traditionally, the radiation source was a radioactive element producing gamma rays, such as Cobalt 60. For reasons of safety, i.e. in the disposal of waste, these systems are now replaced by systems relying on the use of an electron accelerator for producing a high-energy electron beam. This high-energy electron beam then passes through a foil made of a high-Z metal, for producing X-rays.

Typically the product pallets can be carrier-trays of 80×100, 80×120 or 100×120 $cm^2$, (depth×width) on which products may be stacked up to 200 cm. Another kind of products to be irradiated are products under bulk form, such as powder, grains, stored in bags or not. Small packages, such as post parcels having sizes ranging from a few cm to a few tens of cm, having various densities may also be subject to irradiation.

An important family of irradiation systems is related to translation systems, which use a continuous linear conveying of the product before the radiation source. However, this kind of irradiation systems has the drawback that it requires a shielding in the form of a maze which will need a rather important overall space, and a complex transport system along the maze.

Typically, in these irradiation systems, products are stacked either on pallets or on unique carrier trays and maintained in a storage area ahead the irradiation chamber before being conveyed past the radiation source for irradiation of one of their sides. A second pass of the pallets or carriers may be then planned in order to expose their opposite side to the radiation source.

To be efficient, the irradiation system has to provide an even exposure of the product. It is generally admitted that this condition is satisfied if the dose-uniformity ratio also known as "DUR", corresponding to the ratio between the maximum dose and the minimum dose, is as low as possible and preferably is below 2.5.

Different technical solutions have been proposed in the prior art in order to have a uniform irradiation of the product by a translatory movement and then by submitting the products to reorientation means. Examples are given by documents U.S. Pat. No. 4,066,907, U.S. Pat. No. 4,018,348, and GB-A-1206151 wherein complex conveyor systems expose products to a radioactive element such as cobalt-60. The product handling in the device disclosed in these documents is unfortunately very time-consuming as it requires unpacking and repackaging of the product from a pallet to a carrier. All these designs use a radioactive element radiating in all directions of space, and aim at transporting the product around the source, thereby improving the efficiency of radiation capture defined by the throughput.

This problem also exists for the irradiation system disclosed in document U.S. Pat. No. 5,396,074, wherein an overhead transport conveyor is used to hang article carriers and bring them in front of the radiation source, said carriers being able to rotate upon their vertical axes so that both sides of the carriers can be irradiated.

In the particular case of sterilization of low-density products such as medical devices having typically a density comprised between 0.05 and 0.5 and preferably between 0.1 and 0.2 or 0.3, stacked on pallets, the use of X-ray as radiation beam is required.

However, for such kind of products can be place on pallets or carriers, having dimensions of 1.0 m×1.2 m, less than 30% of the X-ray energy is deposited as dose in the product, the remainder traversing the product and being lost. Therefore, in order to optimize the throughput (and therefore to overcome this drawback of loss of radiation beam), several solutions have been suggested. In particular, in WO02/053195 it was suggested to place two parallel lines of pallets in front of the beam, thereby recapturing part of the lost energy. This device requires a complex conveyor system, and control system. Moreover, in order to ensure uniform dose, and avoid dose fall-off at the front and back sides of the first and last pallets of a batch, a large set of similar density pallets must be processed together.

Another family or irradiation systems, i.e. rotation systems, uses means for rotating a product before the radiation source. The irradiator of document U.S. Pat. No. 6,504,898 can be used for such type of irradiation. More particularly, this document is describing an apparatus and process for irradiating a product pallet using a radiation source, an adjustable collimator, a turntable on which the product pallet is loaded, a control system as well as a detection system. The process comprises the steps of (i) determining with the detection system the depth, width, height of the product pallet, as well as the density of the products on said pallet; (ii) adjusting the aperture of the collimator so as to have the required DUR; (iii) rotating the turntable with the product pallet loaded thereon at an adjusted angular velocity in order to have an even DUR factor for the product pallet.

This solution gives good DUR ratios, especially for larger density products, however at the cost of a lower throughput, because an important part of the power is lost in the collimators. Moreover, this system is expensive, because complex control and mechanical handling means are needed for the rotation table and the collimators.

Another drawback of a rotating system is the presence of a excess of dose in the centre of the pallet compared to its surface due to the fact that this centre is always facing the X-ray beam while a portion of the surface is only spending a limited amount of time in front of the target.

Document DD-A-217349 is related to an apparatus for irradiating product pallets with a gamma source. The pallets are arranged on rotating tables and are also able to rotate individually. In the centre of each table is a main source 9, and the rotating tables are arranged around a central additional source 2. The turntables are rotatable in stepwise fashion. This apparatus requires complex combined rotating means for the turntables and for the individual pallets.

Document U.S. Pat. No. 5,001,352 is related to a process and apparatus for irradiating pallets which are arranged around a centrally placed source made of Cobalt 60 rods. The process requires complex movements of the pallets to and from the source. Such manipulations render this method and the apparatus rather complex.

Document GB-A-1206151 is related to an apparatus for irradiating articles, wherein a number of articles is moved around a stationary source.

AIMS OF THE INVENTION

The present invention aims to provide a process and apparatus and a process for irradiating products, which do not present the drawbacks of the devices and processes of the state of the art mentioned here above.

An important aim of the present invention is to optimize the throughput of the installation while maintaining an appropriate dose uniformity ratio (DUR).

A particular aim of the present invention is to provide a process and an apparatus, which allow a uniform irradiation of low density products (densities lower than 0.5 g/cm$^3$) and in particular products such as medical devices having a density lower than 0.3 g/cm$^3$ and requiring an important dose higher than 20 kGray.

The present invention also aims to provide a process and an apparatus, which allow an irradiation of low density products giving a DUR ratio below 2.5.

The present invention also aims to provide a process and an apparatus for performing secured and reliable irradiation with moderate cost in terms of equipment as well as in terms of treatment time.

In particular, the present invention aims to provide a process and an apparatus, which allow simultaneous irradiation of a great quantity of products maintained on pallets or in the bulk form.

SUMMARY OF THE INVENTION

The present invention is related to a process for irradiating products by means of high energy X-ray beam source in an installation having an irradiation chamber, said process comprising the following steps, controlled by controlling means:
  determining the density of the products to be irradiated,
  in order to irradiate said products as a stack predetermining, on the basis of said density, the optimal size of the product stack able to optimize the throughput of the installation and/or the dose uniformity ratio (DUR),
  in the irradiation chamber, loading products as a stack onto rotation means located in front of the X-ray beam source,
  while rotating the rotation means around a rotation axis, irradiating said products from a lateral side of said product stack.

Advantageously, in the present process the rotation speed of the rotation means in front of the radiation beam source is maintained constant.

Preferably, the rotation speed of the rotation means in front of the radiation beam source is maintained constant by the action of the controlling means at a value depending upon predefined parameters.

According to one preferred embodiment, the present process is adapted for irradiating products carried on pallets, characterized in that the stack is formed by at least two contigous pallets.

Preferably, the stack comprises at least four product pallets.

Preferably, in the stack the pallets are in a plane perpendicular to the rotation axis of the rotation means.

According to one preferred embodiment, in the stack four of the product pallets to be irradiated are rectangular product pallets and form together a square base with an open column at the centre of the square base.

Advantageously, in the stack the centre of the square coincides with the rotation axis of the rotation means.

According to one preferred embodiment, in the stack four of the product pallets to be irradiated are rectangular pallets having each at least one corner, and said four product pallets are arranged in such a way that said corner of each pallet coincides in a contact point with one corner of the other three pallets.

Preferably, in the stack the contact point is located on the rotation axis of the rotation means.

According to another preferred embodiment of the invention, the process is adapted for irradiating products under bulk form or under the form of small parcels, characterized in that the product stack is maintained in at least one cylindrical container having an internal volume.

Advantageously, said products are arranged in said cylindrical container so as to fill the total internal volume of said cylindrical container.

In an alternative embodiment, said products are arranged in said cylindrical container so as to let an open column along the center axis of the cylindrical container.

Preferably, said cylindrical container is selected from a set of cylindrical containers such as tons or cylindrical baskets, having a diameter near to said determined optimal size.

Preferably, in the process of the invention, the irradiation of the products is performed by batches of products of similar densities.

Another object of the invention concerns an apparatus for irradiating products, said apparatus comprising:
  a high energy X-ray beam source, for irradiating the products from a lateral side with a beam directed along a first direction substantially perpendicular to said lateral side, and scanned along a second direction substantially perpendicular to said first direction,
  an irradiation chamber, where irradiation of the products can be performed, said irradiation chamber comprising rotation means for rotating said products around a rotation axis parallel to said second direction,
  rotation means for rotating said products in front of said X-ray beam source at a constant rotation speed, around said rotation axis, during irradiation, said rotation means comprising means for receiving the products;

said apparatus being characterized in that said means for receiving the products are adapted to receive products loaded thereon as a stack the size of which is variable depending on the density of said products.

According to one preferred embodiment, said apparatus is adapted to receive a product stack comprising products carried on pallets.

Preferably, the rotations means are adapted to receive a product stack comprising at least two contigous pallets.

Preferably, the rotation means are adapted to receive a product stack comprising at least four product pallets.

Advantageously, in the present apparatus, the rotation means are adapted to receive a product stack wherein said product pallets are arranged relatively to each other in the same plane perpendicular to the rotation axis of the rotation means.

According to one preferred embodiment, the rotation means are adapted to receive a stack wherein four of the product pallets to be irradiated are rectangular product pallets and form together a square base with an open column at the centre of the square base.

Preferably, the rotation means are adapted to receive a stack wherein the centre of the square coincides with the rotation axis of the rotation means.

According to another preferred embodiment, the rotation means of the present apparatus are adapted to receive a stack wherein four of the product pallets to be irradiated are rectangular pallets having each at least one corner, and said four product pallets are arranged in such a way that said corner of each pallet coincides in a contact point with one corner of the other three pallets.

Preferably, the rotation means are adapted to receive a stack wherein the contact point is located on the rotation axis (10) of the rotation means.

According to another embodiment, the rotation means the apparatus are adapted to receive a product stack wherein the products are under bulk form or under the form of small parcels.

Preferably, the rotation means are adapted to receive a product stack wherein the product stack is maintained in at least one cylindrical container such as a ton or a cylindrical basket.

Preferably, the means in the rotation means for receiving the product stack comprise a turntable.

Advantageously, the apparatus of the present invention further comprises controlling means for controlling the overall operating state of the apparatus.

Preferably, said controlling means are able to control the rotation speed of the rotation means.

Preferably, said controlling means are able to maintain constant the rotation speed of the rotation means, the value of said rotation speed being dependent upon predefined parameters.

Preferably, the apparatus according to the invention can operate for irradiation of the products by batches of products of similar densities.

SHORT DESCRIPTION OF THE DRAWINGS

FIG. 3b corresponds to a side view of the irradiation apparatus according to the same embodiment as in FIG. 1a.

FIGS. 8a and 9a give the performances obtained with an irradiation apparatus of the present invention using rotation means having a load capacity of four product pallets (see the reference "Rotating/4-pallets"). Said performances are compared with the performances of irradiation apparatus according to the state of the art and using (i) rotation means having a load capacity of one product pallet (see curve with the reference "Rotating/1 pallet"), (ii) a double-sided two-row irradiation system or (iii) a double-sided single-row irradiation system.

More precisely, FIG. 8a gives the throughput of the installation as a function of the density of the product irradiated with a minimum dose ($D_{min}$) of 25 kGray and an irradiation energy of 5 MeV, and beam power of 500 KW.

DETAILED DESCRIPTION OF SEVERAL PREFERRED EMBODIMENTS OF THE INVENTION

In the following description, it is meant by "stack" or "product stack" the products with their carrier (pallet or container).

When irradiating a product stack from the lateral side with an X-ray beam, two considerations have to be taken into account: first, in order to achieve effective sterilization, a minimal dose must be deposited throughout the volume of the product stack. Owing to the properties of X-rays, dose deposition will not be uniform, and some of the areas will receive a larger dose. This non-uniformity is qualified by the "Dose Uniformity Ratio" (DUR) which is the ratio of the maximal dose deposited in the volume to the minimal dose deposited in the volume. It is desirable that this ratio be as near to one as possible, and preferably below 2.5.

A second consideration in the design of an irradiation system is the throughput of the installation. The throughput of the installation can be defined as the volume of material per unit time that can be processed up to a given dose. This throughput depends on the size of the product stack. For smaller sizes, the throughput is low because a large part of the X-ray energy traverses the product, and is lost. For larger sizes, a long irradiation is necessary for reaching the minimal dose in the centre of the product stack. This leads to a higher dose at the surface of the product stack, and hence a higher DUR, and reduced throughput. In between these extremes, an optimal size maximizes throughput.

Figure 1A:
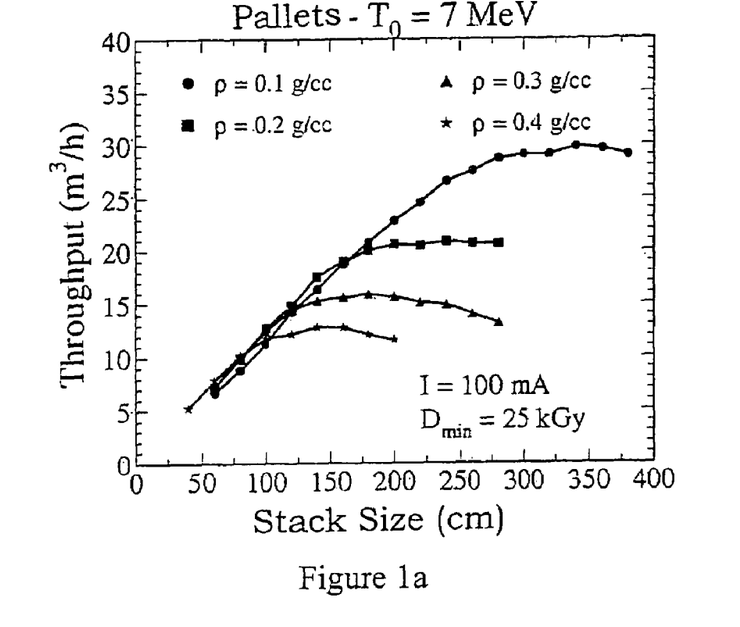
FIG. 1a gives the throughput of the installation as a function of the size of the product stack for a product stack having a square basis, for different product mean densities.
Figure 1B:
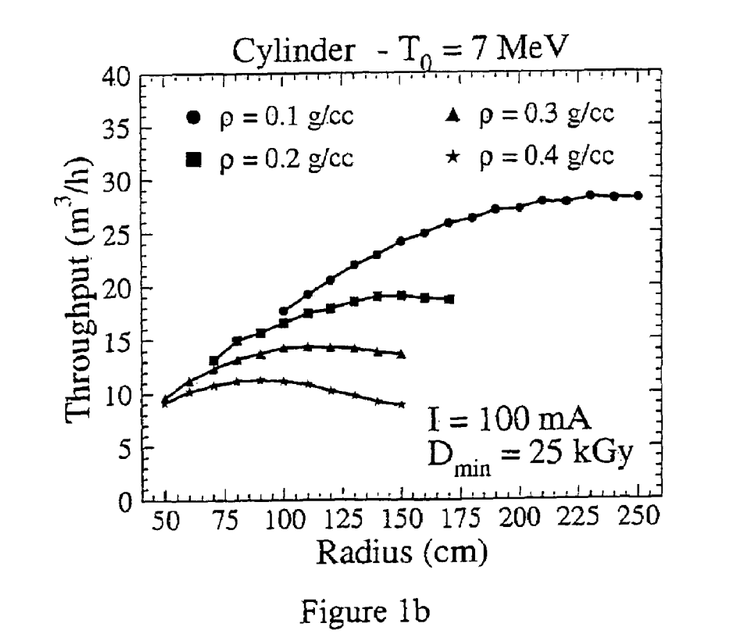
FIG. 1b gives the same, for a product stack consisting in one cylindrical container.

FIGS. 1a and 1b are obtained as follows: for a given product mean density (respectively 0.1, 0.2, 0.3, 0.4 g/cm3), one irradiates product stacks increasing sizes L. The size L is either the side of a stack consisting of square pallets (FIG. 1a), or the radius of a stack consisting of a cylindrical container (FIG. 1b). One irradiates for obtaining everywhere in the product stack at least a given minimal dose, e.g. 25 kGy. From the required duration for obtaining this minimal dose, the throughput is determined. This throughput varies as a function of size L, and shows a maximum. This maximum is the optimal stack size for the given product density.

Figure 2A:
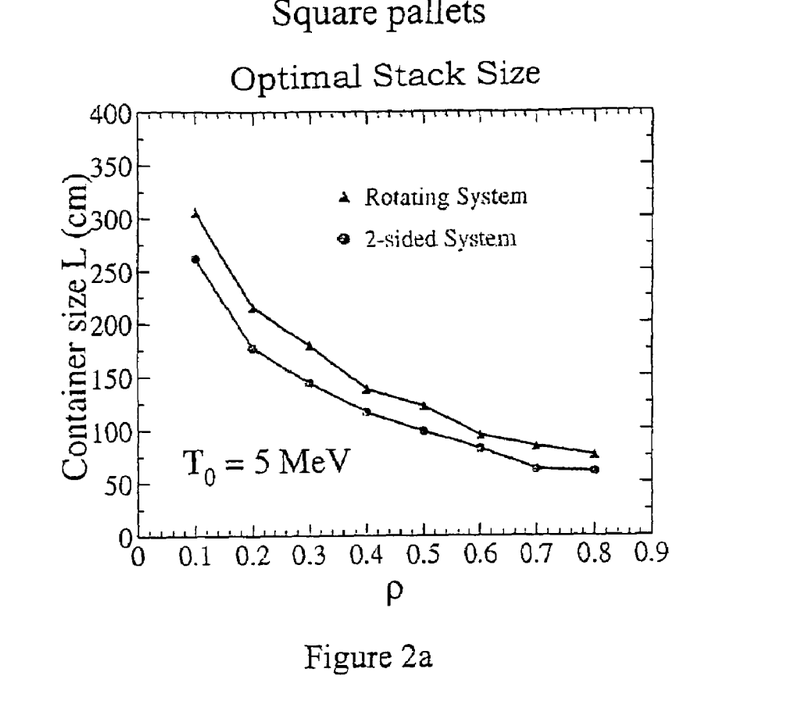
FIG. 2a gives the evolution of the optimal size of a product stack made of four pallets as a function of the product density for the irradiation apparatus of the invention including rotation means and for a translation irradiation apparatus of the state of the art including a double-side irradiation system.
Figure 2B:
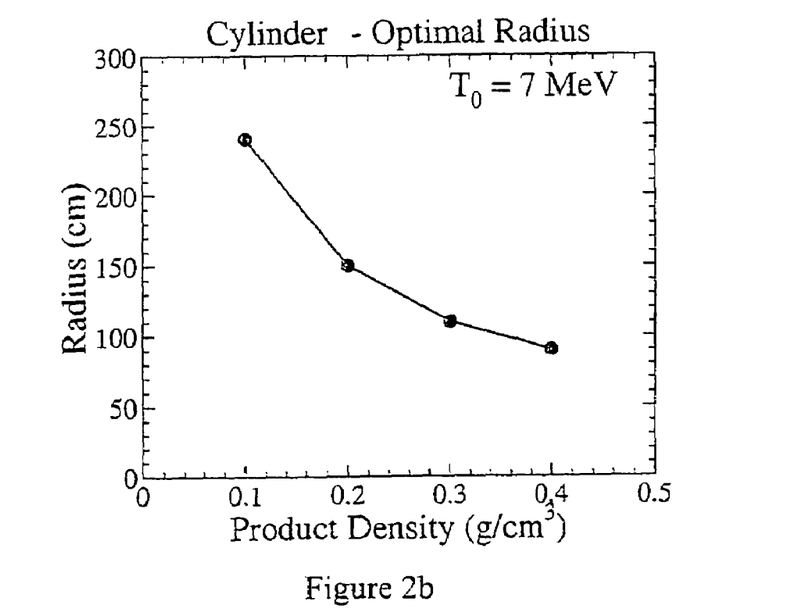
FIG. 2b gives the evolution of the optimal radius of a product stack consisting in one cylindrical container as a function of the product density for the irradiation apparatus of the invention.
Figure 7:
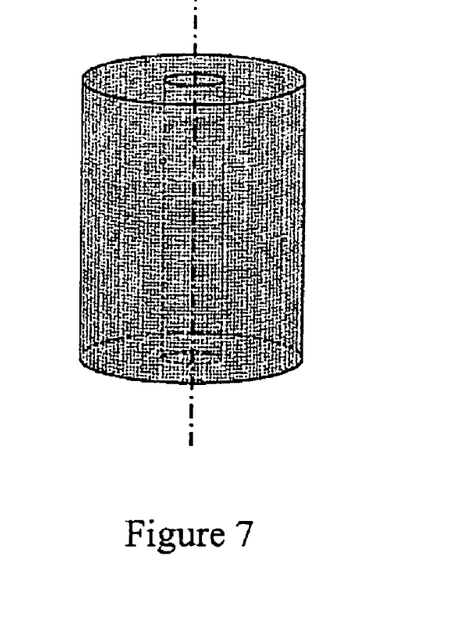
FIG. 7 represents another preferred embodiment for a product stack adapted for the irradiation of products under bulk form or small parcels consisting in one cylindrical container having an open column along its main axis (centre axis).

This optimal stack size is plotted as a function of product density on FIG. 2a (square pallets) and FIG. 2b (cylindrical containers). In addition, FIG. 7a shows the optimal stack size for an irradiation system having a translatory movement of the products, and a 180° rotation for performing a double-side irradiation. As can be seen from the drawings (FIGS. 2a and 2b), the optimal stack size varies with product density. The optimal size for a square product pallet having a density of 0.2 is 220 cm, for a rotating system. For a cylindrical container containing product having mean density of 0.2 g/cm3, the optimal radius is 150 cm.

Figure 3A:
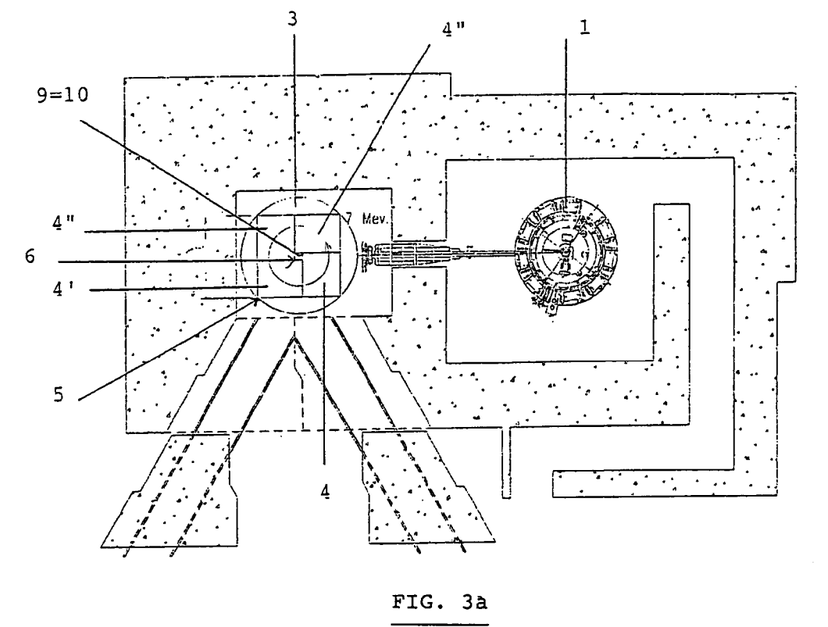
FIG. 3a represents a general top view of an irradiation apparatus according to one embodiment of the present invention.
Figure 3B:
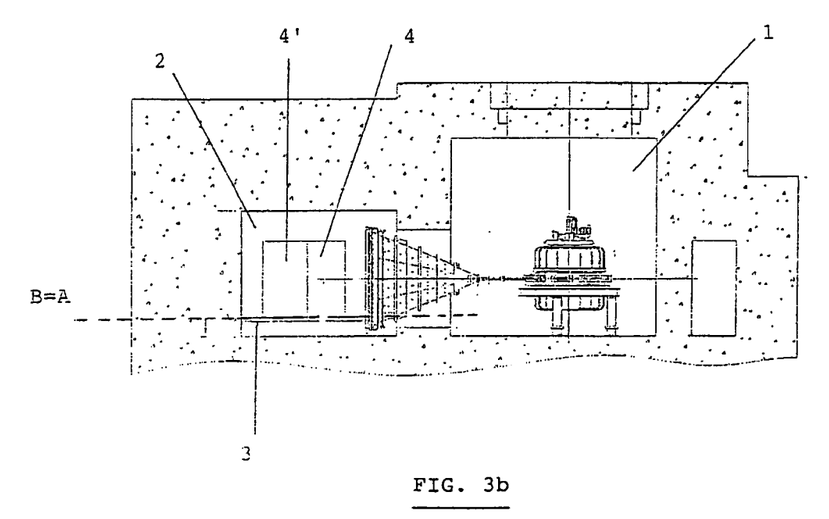

The apparatus shown in FIGS. 3a and 3b comprises:
- a protective shielding;
- a source 1 able to emit a high energy electron beam, said electron beam being directed to a foil of high-Z material for producing X-rays;
- an irradiation chamber 2 where irradiation may take place;
- rotation means 3 included inside the irradiation chamber 2 and located in front of the radiation beam source 1.

The invention mainly concerns a method and an apparatus as shown in FIG. 3, characterized by the fact that the rotation means is capable of carrying a set of products to irradiate in the form of a product stack and rotate this set in front of the irradiation source according to one preferred embodiment the products are contained on pallets.

Preferably said product stack consists in at least two pallets.

This means that the products are rotated in such a way that they do not rotate relatively with respect to each other. They are rotated and irradiated as a whole. Furthermore, the set of products is irradiated as a stack from the lateral side, contrary to prior art installations where the pallets are rotated individually and/or around a centrally placed irradiation source. In the apparatus of the invention, the source is located next to the set of pallets, not in between them. The invention is further related to optimum ways of arranging the pallets in the plane perpendicular to the rotation axis, in order to obtain an optimum DUR characteristic. The pallets are rotated at a constant speed. This obviates the need for complex speed control means in an apparatus of the invention. The apparatus of the invention also does not require a collimator.

According to another embodiment, the rotating means of the apparatus is adapted to carry one single container, containing products in bulk. This container may have a cylindrical form 11 as shown in FIG. 6 and FIG. 7 and according to a preferred embodiment shown on FIG. 7, this cylindrical container 11 has an inner wall 12 and an outer wall 13, wherein the products in bulk are present in the space between the two walls 12,13 thereby creating an empty column 6 in the centre of the container 11. The effect of the empty column 6 is to optimize the dose uniformity in the same way as explained for the open column 6 in the embodiment of FIG. 5.

The rotation means 3 may comprise a turntable, but could be other suitable rotation means. One defines for the turntable 3 a plane A.

The method and apparatus of the invention allow a number of pallets to be irradiated simultaneously as a stack by successive penetration of the beam into each pallet of the set of pallets arranged before the source.

Figure 4:
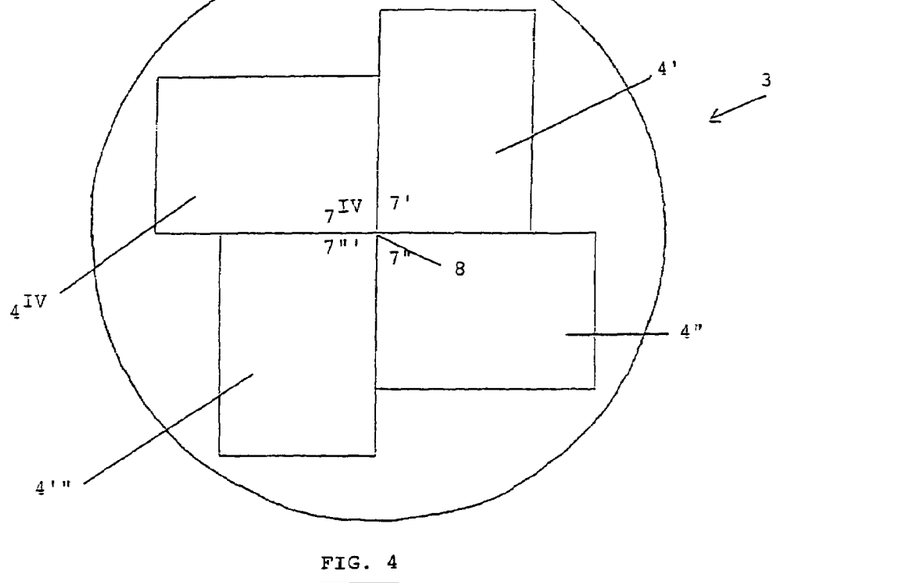
FIG. 4 represents a product stack with a relative arrangement of four product pallets as loaded on rotation means according to one preferred embodiment in the apparatus of the present invention.
Figure 5:
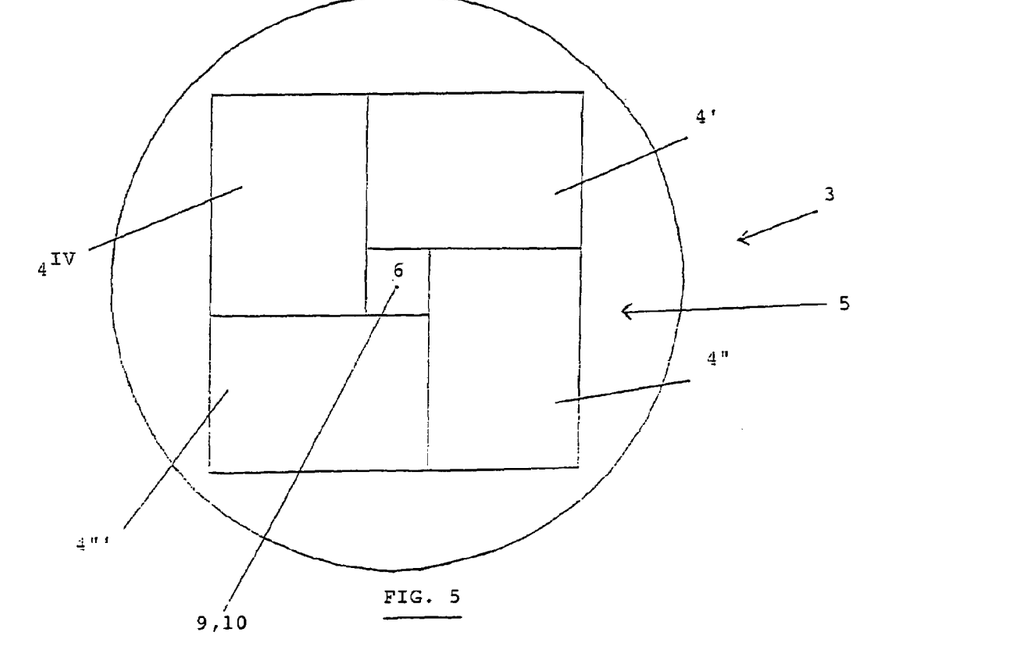
FIG. 5 represents a product stack with a relative arrangement of four product pallets as loaded on rotation means according to another preferred embodiment in the apparatus of the present invention.
Figure 6:
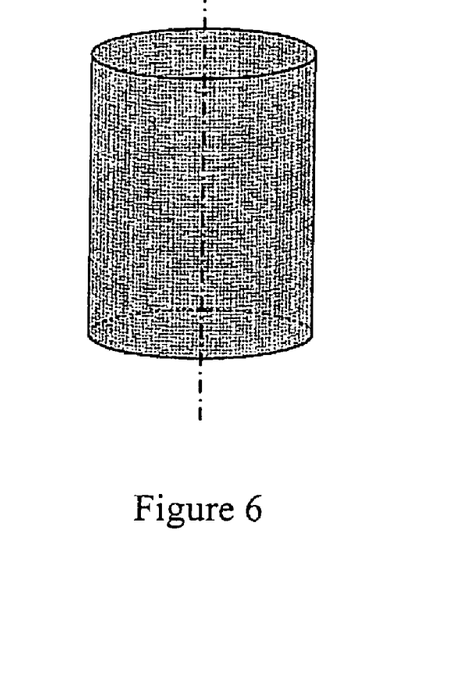
FIG. 6 represents another preferred embodiment for a product stack adapted for the irradiation of products under bulk form or small parcels consisting in one cylindrical container.

In the preferred embodiments of FIGS. 4 and 5, four rectangular based product pallets 4, 4', 4", 4''' are placed as product stack on the turntable 3 in a same plane B, which is parallel to the plane A of the turntable 3. As illustrated on FIG. 3a, and detailed in FIG. 5, the four pallets 4, 4',4", 4''' are arranged relatively to each other to form together a square base 5 with an open column 6 at the centre 9 of the square. Preferably, said centre 9 coincides with the centre 10 of the turntable 3. One advantage of said configuration is that the problem that the products receive a dose higher than required which is a problem associated to classical irradiation apparatus is avoided here, as the area where this over-irradiation occurs precisely corresponds to the hole or open column 6, where there is no matter.

One advantage of said configuration is that the dose increase at the centre of the product observed in rotating systems is partly avoided here.

An alternative possible embodiment for arranging four pallets as a stack on the rotation means (turntable) 3 is illustrated on FIG. 4. In said embodiment, one defines for each pallet 4, 4', 4", 4''' one corner 7, 7', 7", 7''' respectively and the pallets are arranged so that said corners 7, 7', 7", 7''' coincide with each other at a contact point 8. Preferably, said contact point 8 coincides with the centre 10 of the turntable 3.

According to the invention, different conveying means as known in the state in the art, could be used in order to convey the product pallets 4, 4', 4", 4''' inside, and once irradiated, outside the irradiation chamber 2.

For example, the conveying could be done by horizontal and/or vertical translation conveying means. Another possibility is to use rotation means such as revolving doors as disclosed in the document EP1340512 (published after priority date of the present application). In this example, the turntable 3 may have a diameter of about 3 metres and the revolving door may have a width of about 3.5 metres.

Similarly, different means known in the state of the art could be envisaged for loading the product pallets 4, 4', 4", 4''' on the rotation means 3. It could be horizontal such as a fork-lift, or vertical loading means such as a travelling crane. The loading of the pallets onto the turntable 3 could be done pallet by pallet or with several pallets together.

Different means may be used for entering and removing the product pallets in/from the irradiation chamber 2. A sliding door, as shown on FIGS. 1a and 1b may be used, leaving space for entering with a simple forklift. As an alternative, a revolving door, as disclosed in EP1340512 may be used. When loading/unloading from above with a travelling crane, the shielding may comprise a moveable concrete lid.

Moreover, the operating state of the apparatus as a whole, and in particular of the irradiation process, is under the control of controlling means. Advantageously, said controlling means act so as to allow the irradiation of the product pallets only when said pallets are loaded as a stack on the rotation means 3 and only when the rotation means are rotating.

In addition, the controlling means are conceived so as to control the rotation speed of the rotation means 3. Preferably, the rotation speed is maintained constant by the controlling means, at a value defined by specific parameters, including the product density.

The pallets 4, 4', 4", 4''' used herein are standard pallets, typically 100×120×180 cm$^3$ (depth/width/height). Other conventional pallet sizes may be used, as well as other types of supports, such as bags, or bins.

An important characteristic of the present invention is that the apparatus and the irradiation process related thereto are conceived so as to achieve a high throughput and to maximize the dose uniformity between the centre of the pallets 4, 4', 4", 4''' and their sides.

For this purpose, the rotation means as used in the present invention are advantageously used in a compact batch X-ray apparatus. This means that product pallets can be treated in batches and the conveying system is optimized in length and in speed so as to have a high throughput and profitability of the apparatus (beam time).

The apparatus according to the invention is particularly suitable for the irradiation of products such as medical devices, said products having a low density (lower than 0.5) and requiring irradiation doses of about 20 kGray in order to have a reliable sterilization. Indeed, the times for loading the pallets onto the rotation means 3 are very short (a few minutes) comparatively to the treatment (irradiation) time (several hours).

Another advantage of the apparatus of the present invention is that it is very simple to use because no collimator and no variation of the rotation speed of the turntable are necessary for having a satisfying irradiation of the products. In addition, said characteristics contribute to the optimization of the treatment time and of the throughput.

As illustrated on FIG. 8a to 9b, the apparatus according to the present invention presents very satisfying performances for irradiating products of low density comparatively to other irradiation apparatus of the state of the art.

Figure 8A:
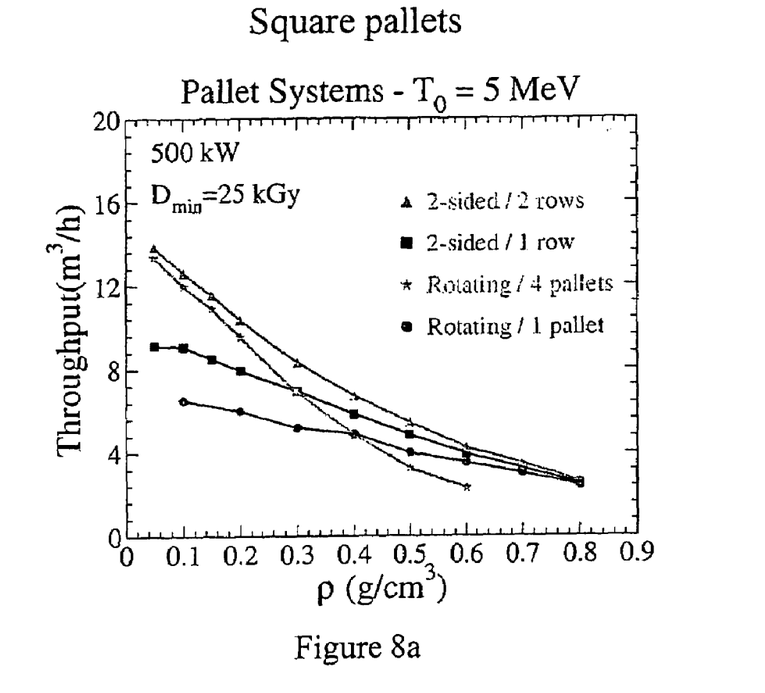
Figure 8B:
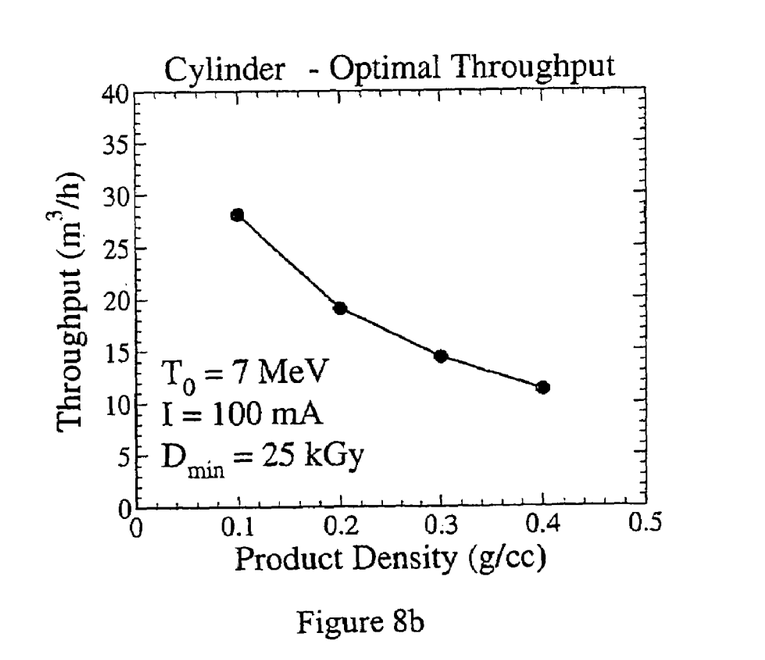
FIGS. 8b and 9b give the performances of the installation (throughput and DUR, respectively) as a function of the density of the product irradiated at an irradiation energy of 7 MeV.
Figure 9A:
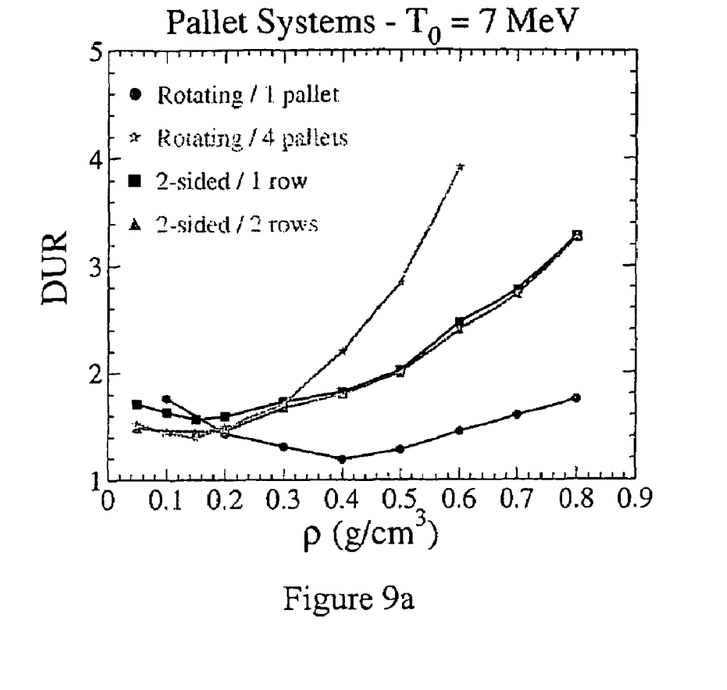
Figure 9B:
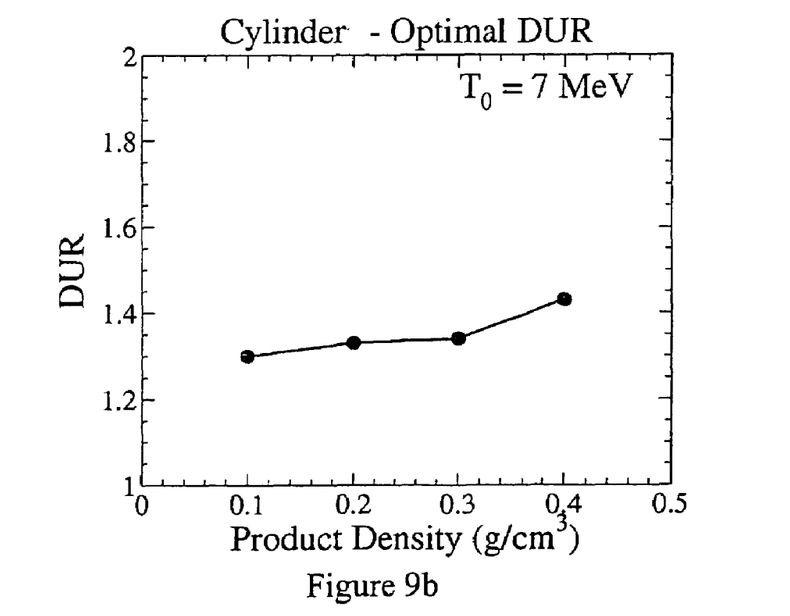

In particular, from FIGS. 8a and 8b, it can be observed that the best DUR is clearly obtained with the apparatus including rotation means, and especially with the apparatus of the invention, for product densities below 0.2

Moreover, as shown on FIGS. 2a and 2b, for densities below 0.2, the 4-pallet rotating system of the present invention exhibits treatment capacity comparable to a 2-row double-sided irradiation system. Given the fact that the 4-pallet rotating system as in the present invention is surely less costly to build and easier to use than a 2-row double-sided irradiation system, the apparatus of the invention is an attractive solution for a compact batch system when coupled to a lower power machine, as for example the one sold by the Applicant with the reference "TT100".

Using the design of the present invention, a compact and efficient irradiation system may be built, using a footprint not larger than the currently used ETO systems. In contrast with the prior art translation systems, an irradiation session may be started once two or four pallets are ready for treatment, whereas in the prior art designs, many pallets must be grouped before being processed together. In contrast to the prior art rotation systems, no collimators, nor variable speed rotation means are required. For a given installation, a single parameter selection is required, i.e. the processing time. This processing time is being selected as a function of the required minimal dose. The use of the apparatus is therefore very simple. A typical irradiation, for achieving a minimal dose of 25 kGy, is taking two hours. For typical rotation means rotating at one turn per minute, this means that 120 turns have been made at the end of the irradiation. Therefore, no precise synchronization is required in order to ensure that a whole number of turns are performed, because such an error would produce a dose error less that one percent, in a sector of the product. The required control system is therefore very simple.

List of Numerical References Used in the Description
1. X-ray beam source
2. Irradiation chamber
3. Rotation means
4. 4', 4", 4''', 4$^{IV}$ Product pallets
5. square base
6. open column or empty column
7. corner
8. contact point
9. centre of square
10. centre of turntable
11. cylindrical container
12. inner wall of cylindrical container
13. outer wall of cylindrical container

The invention claimed is:

1. A process for irradiating products by means of a high energy X-ray beam source in an installation having an irradiation chamber, said process comprising the steps of:
determining the density of the products to be irradiated,
in order to irradiate said products as a stack, predetermining, on the basis of said density, the optimal size of the product stack able to optimize the throughput of the installation and/or the dose uniformity ratio (DUR),
in the irradiation chamber, loading products as a stack of said optimal size onto rotation means located in front of the X-ray beam source,
while rotating the rotation means around a rotation axis, irradiating said products from a lateral side of said product stack without using a collimator wherein said steps are controlled by a controlling means.

2. The process according to claim 1, wherein the rotation speed of the rotation means in front of the X-ray beam source is maintained constant.

3. The process according to claim 2, wherein the rotation speed of the rotation means in front of the radiation beam source is maintained constant by the action of the controlling means at a value depending upon predefined parameters.

4. The process according to claim 1, wherein the products are carried on pallets and the stack is formed by at least two contiguous pallets.

5. The process according to claim 4 wherein the stack comprises at least four product pallets.

6. The process according to claim 1 wherein the pallets in the stack are in a plane perpendicular to the rotation axis of the rotation means.

7. The process according to claim 5 wherein the four product pallets to be irradiated are rectangular product pallets and form together a square base with an open column at the centre of the square base.

8. The process according to claim 7, wherein the centre of the square coincides with the rotation axis of the rotation means.

9. The process according to claim 5 wherein the four product pallets to be irradiated are rectangular pallets having each at least one corner, and said four product pallets are arranged in such a way that said corner of each pallet coincides in a contact point with one corner of the other three pallets.

10. The process according to claim 9 wherein the contact point is located on the rotation axis of the rotation means.

11. The process according to claim 1, adapted for irradiating products under bulk form or under the form of small parcels, wherein the product stack is maintained in at least one cylindrical container having an internal volume.

12. The process according to claim 11, wherein said products are arranged in said cylindrical container so as to fill the total internal volume of said cylindrical container.

13. The process according to claim 11, wherein said products are arranged in said cylindrical container so as to let an open column along the center axis of the cylindrical container.

14. The process according to claim 11, wherein said cylindrical container is selected from a set of cylindrical containers consisting of mortars and cylindrical baskets, said cylindrical containers having a diameter near to said determined optimal size.

15. The process according to claim 1, wherein the irradiation of the products is performed by batches of products of similar densities.

16. An apparatus for irradiating products, said apparatus comprising:
   a high energy X-ray beam source, for irradiating the products from a lateral side with a beam directed along a first direction substantially perpendicular to said lateral side, and scanned along a second direction substantially perpendicular to said first direction,
   an irradiation chamber, where irradiation of the products can be performed, said irradiation chamber comprising rotation means for rotating said products around a rotation axis parallel to said second direction,
   said rotating taking place in front of said X-ray beam source at a constant rotation speed, during irradiation, said rotation means comprising means for receiving the products;
   wherein said apparatus does not comprise a collimator, and said means for receiving the products are adapted to receive products loaded thereon as a stack the size of which is variable depending on the density of said product,
   wherein said apparatus is adapted to receive a product stack comprising products carried on pallets,
   wherein the product stack comprises at least four contiguous pallets,
   wherein that at least four product pallets to be irradiated are rectangular pallets having each at least one corner and said four product pallets are arranged in such a way that said corner of each pallet coincides in a contact point with one corner of the other three pallets,
   and wherein the contact point is located on the rotation axis of the rotation means.

17. An apparatus for irradiating products, said apparatus comprising:
   a high energy X-ray beam source, for irradiating the products from a lateral side with a beam directed along a first direction substantially perpendicular to said lateral side, and scanned along a second direction substantially perpendicular to said first direction,
   an irradiation chamber, where irradiation of the products can be performed, said irradiation chamber comprising rotation means for rotating said products around a rotation axis parallel to said second direction,
   said rotating taking place in front of said X-ray beam source at a constant rotation speed, during irradiation, said rotation means comprising means for receiving the products;
   wherein said apparatus does not comprise a collimator, and said means for receiving the products are adapted to receive products loaded thereon as a stack the size of which is variable depending on the density of said products,
   wherein said apparatus is adapted to receive a product stack comprising products carried on one or more pallets, wherein each of said one or more product pallets to be irradiated comprises one corner and a contact point and said contact point is located on the rotation axis of the rotation means and the corner and contact point of said one or more product pallets coincides.

* * * * *